(12) United States Patent
Marino et al.

(10) Patent No.: US 7,087,072 B2
(45) Date of Patent: Aug. 8, 2006

(54) ARTICULATED CENTER POST

(75) Inventors: Joseph A. Marino, Apple Valley, MN (US); Michael P. Corcoran, Oakdale, MN (US)

(73) Assignee: Cardia, Inc., Burnsville, MN (US)

( * ) Notice: Subject to any disclaimer, the term of this patent is extended or adjusted under 35 U.S.C. 154(b) by 212 days.

(21) Appl. No.: 10/348,865

(22) Filed: Jan. 22, 2003

(65) Prior Publication Data

US 2004/0143293 A1    Jul. 22, 2004

(51) Int. Cl.
    *A61B 17/04* (2006.01)
(52) U.S. Cl. ........................................ 606/213
(58) Field of Classification Search ............... 606/213, 606/215
    See application file for complete search history.

(56) References Cited

U.S. PATENT DOCUMENTS

| | | | |
|---|---|---|---|
| 3,874,388 A | 4/1975 | King et al. | |
| 4,007,743 A | 2/1977 | Blake | 128/334 |
| 4,284,166 A | 8/1981 | Gale | |
| 4,917,089 A | 4/1990 | Sideris | 606/215 |
| 5,092,424 A | 3/1992 | Schreiber et al. | |
| 5,108,420 A | 4/1992 | Marks | 606/213 |
| 5,171,259 A | 12/1992 | Inoue | 606/213 |
| 5,284,488 A | 2/1994 | Sideris | 606/213 |
| 5,334,137 A | 8/1994 | Freeman | 604/8 |
| 5,334,217 A | 8/1994 | Das | 606/213 |
| 5,382,260 A | 1/1995 | Dormandy, Jr. et al. | 606/151 |
| 5,397,331 A | 3/1995 | Himpens et al. | 606/151 |
| 5,425,744 A | 6/1995 | Fagan et al. | 606/213 |
| 5,433,727 A | 7/1995 | Sideris | 606/213 |
| 5,451,235 A | 9/1995 | Lock et al. | 606/213 |
| 5,634,936 A | 6/1997 | Linden et al. | 606/213 |
| 5,702,421 A | 12/1997 | Schneidt | 606/213 |
| 5,709,707 A | 1/1998 | Lock et al. | 606/213 |
| 5,725,552 A | 3/1998 | Kotula et al. | 606/213 |
| 5,741,297 A | 4/1998 | Simon | 606/213 |
| 5,904,703 A | 5/1999 | Gilson | 606/213 |
| 6,024,756 A | 2/2000 | Huebsch et al. | 606/213 |
| 6,174,322 B1 | 1/2001 | Schneidt | 606/213 |
| 6,206,907 B1 | 3/2001 | Marino et al. | 606/215 |
| 6,379,368 B1 | 4/2002 | Corcoran et al. | 606/153 |
| 6,389,146 B1 | 5/2002 | Croft, III | |
| 6,551,344 B1 * | 4/2003 | Thill | 606/213 |
| 6,634,455 B1 | 10/2003 | Yang | |

FOREIGN PATENT DOCUMENTS

| | | |
|---|---|---|
| DE | 233 303 | 2/1986 |
| DE | 42 22 291 C1 | 1/1994 |
| EP | 0 362 113 | 4/1993 |
| EP | 0 541 063 | 9/1998 |
| GB | 2 269 321 A | 9/1994 |

* cited by examiner

*Primary Examiner*—Gary Jackson
(74) *Attorney, Agent, or Firm*—Kinney & Lange, P.A.

(57) ABSTRACT

This invention relates to an occlusion device for the heart, having an articulated center post which allows the device to better conform to the contours of the heart to increase sealing abilities and reduce breakage resulting from conformation pressure.

12 Claims, 8 Drawing Sheets

ARTICULATED CENTER POST

CROSS-REFERENCE TO RELATED APPLICATION(S)

This application is related to U.S. patent application entitled Hoop Design for Occlusion Device, Ser. No. 10/349,118, Occlusion Device Having Five or More Arms, Ser. No. 10/348,701, Septal Stabilization Device, Ser. No. 10/349,744, and U.S. patent application entitled Laminated Sheets for use in a Fully Retrievable Occlusion Device, Ser. No. 10/348,864, all filed on even date herewith.

BACKGROUND OF THE INVENTION

This invention relates to an occlusion device for the closure of physical apertures, such as vascular or septal apertures. More specifically, this invention relates to an occlusion device for the heart, having an articulated center post which allows the device to better conform to the contours of the heart.

Normally, permanently repairing certain cardiac defects in adults and children requires open heart surgery, a risky, expensive, and painful procedure. To avoid the risks and discomfort associated with open heart surgery, modern occlusion devices have been developed that are small, implantable devices capable of being delivered to the heart through a catheter. Rather than surgery, a catheter inserted into a major blood vessel allows an occlusion device to be deployed by moving the device through the catheter. This procedure is performed in a cardiac cathlab and avoids the risks and pain associated with open heart surgery. These modern occlusion devices can repair a wide range of cardiac defects, including patent foramen ovale, patent ductus arteriosus, atrial septal defects, ventricular septal defects, and may occlude other cardiac and non-cardiac apertures.

There are currently several types of occlusion devices capable of being inserted via a catheter including button devices, collapsible umbrella-like structures, and plug-like devices. A potential draw back to these devices is the difficulty in ensuring that the occluder conforms to the contours of the defect. Poor conformation to the defect results in poor seating of the device which decreases the ability of the device to occlude the defect. Ensuring the proper seating of an occlusion device once it has been deployed poses a continuing challenge given the uneven topography of the vascular and septal walls of each patient's heart. The challenge in designing an occluder which conforms to the uneven topography is compounded by the fact that the contours of each defect in each individual patient are unique.

Lack of conformation to the walls of the heart can place significant amounts of stress on the occlusion device and decrease fatigue life. Once deployed, different parts of the occluder may experience more or less stress as a result of the uneven topography. At some point, stressed parts of the occluder may break. Broken parts increase the likelihood of damage to the surrounding tissue and lead to patient anxiety.

Thus, there is a need in the art for an occlusion device that will occlude cardiac defects and will match the contours of the heart thereby increasing the life of the device and sealing ability while reducing damage the surrounding tissue.

BRIEF SUMMARY OF THE INVENTION

The present invention allows occlusion devices to more effectively close a physical anomaly. The present invention is an occlusion device having an articulated center section. The articulated center section increases the ability of the occlusion device to more accurately conform to the defect. The center section may consist of a post having left and right parts and a joint which links the left and right parts and provides articulation. Any joint or hinge could be used to join the left and right sides. One suitable joint is a ball joint.

DETAILED DESCRIPTION

Figure 1:
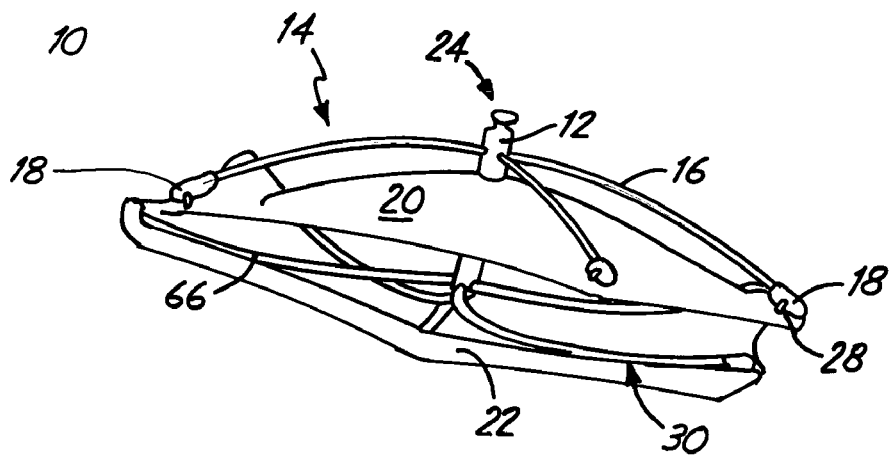
FIG. 1 is a perspective view of an occlusion device with an articulated center post.

FIG. 1 is a top perspective view of an occlusion device 10. As viewed in FIG. 1, the device 10 comprises a center section 12, proximal and distal fixation devices 14, 30 (each comprised of six arms 16), atraumatic tips 18, an proximal sheet 20, and a distal sheet 22. The proximal and distal fixation devices 14, 30 are attached to the sheets 20, 22 using sutures 28. The proximal and distal fixation devices 14, 30 are connected to the center post 12. One method of connecting the arms 16 to the post 12 is to provide the center post 12 with drill holes through which the arms 16 extend. The atraumatic tips 18 are located at the distal end of each arm 16 and serve to minimize damage to the surrounding tissue. The atraumatic tips 18 provide a place for the sutures 28 to attach the sheets 20, 22 to the proximal and distal fixation devices 14, 30. One method of suturing the sheets 20, 22 to the proximal and distal fixation devices 14, 30 is to provide the atraumatic tips 18 with drill holes through which the sutures 28 pass. In this way, the sheets 20, 22 are sewn to the fixation devices 14, 30 at the atraumatic tips 18. More specifically, the occlusion device 10 is constructed so that the proximal and distal fixation devices 14, 30 are easily collapsible about the center section 12. Due to this construction, the occlusion device 10 can be folded so that the fixation devices 14, 30 are folded in the axial direction. The proximal and distal sheets 20, 22 attached to the proximal and distal fixation devices 14, 30 are flexible, and can likewise collapse as the proximal and distal devices 14, 30 are folded. In addition, the center post 12 further comprises a knob 24. The knob 24 allows for the device 10 to be grasped as it is inserted into the body through the catheter.

Once the device 10 is deployed, the fixation devices 14, 30 serve to hold the proximal and distal sheets 20, 22 in place to seal the defect. To ensure there is sufficient tension to hold the sheets 20, 22 in place, the fixation devices 14, 30 are made of a suitable material capable of shape memory, such as nickel-titanium alloy, commonly called Nitinol. Nitinol is preferably used because it is commercially available, very elastic, non-corrosive and has a fatigue life greater than that of stainless steel. To further ensure that the fixation devices 14, 30 do not suffer from fatigue failures, one embodiment of the present invention relies on making the wire fixation devices 14, 30 of stranded wire or cables.

The center section 12 shown in the device 10 is articulated. The articulation can be accomplished by a variety of methods. The articulation could comprise one or more joints, or hinges. It could also be a spring or a coil. Additionally, a spot specific reduction in the amount of material used to create the center section 12 could render portions of the section 12 sufficiently flexible.

The center section 12 is preferably formed to have a diameter of between about 8 millimeters and about 0.1 millimeters. In addition, the length of the center section is preferably less than about 20 millimeters.

The sheets 20, 22 are comprised of a medical grade polymer in the form of film, foam, gel, or a combination thereof. One suitable material is DACRON®. Preferably, a high density polyvinyl alcohol (PVA) foam is used, such as that offered under the trademark IVALON®. To minimize the chance of the occlusion device 10 causing a blood clot, the foam sheets 20, 22 may be treated with a thrombosis inhibiting material. One such suitable material is heparin.

The size of the sheets 20, 22 may vary to accommodate various sizes of defects. When measured diagonally, the size of the sheets 20, 22 may range from about 15 millimeters to about 45 millimeters. In some instances, it may be desirable to form the sheets 20, 22 so that they are not both the same size. For instance, one sheet and its associated fixation device can be made smaller (25 millimeters) than the corresponding sheet and its associated fixation device (30 millimeters). This is particularly useful in situations where the occlusion device 10 is to be placed at a location in the heart which is close to other nearby cardiac structures. Making the sails 20, 22 different sizes may assist in providing optimal occlusion of a defect, without affecting other structures of the heart which may be nearby.

Figure 2A:
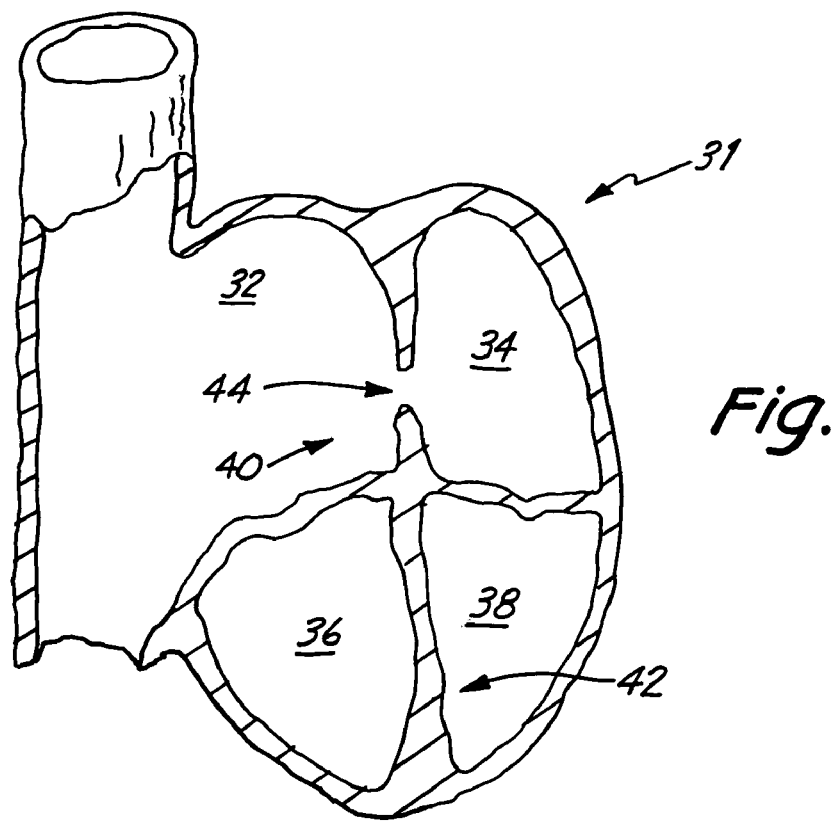
FIG. 2A is a diagram of the heart.

FIGS. 2A through 2D illustrate the method by which the occlusion device 10 is deployed. FIG. 2A is a diagrammatic view of a human heart 31. Visible in FIG. 2A is the right atrium 32, the left atrium 34, the right ventricle 36, the left ventricle 38. The right atrium 32 is separated from the left atrium 34 by a atrial septal wall 40. The right ventricle 36 is separated from the left ventricle 38 by a ventricular septal wall 42. Also visible in FIG. 2A is an atrial septal defect 44 located in the atrial septal wall 40, between the right atrium 32 and left atrium 34 of the heart 31. An atrial septal defect 44 is one example of a cardiac defect that may be occluded using the occlusion device 10.

Figure 2B:
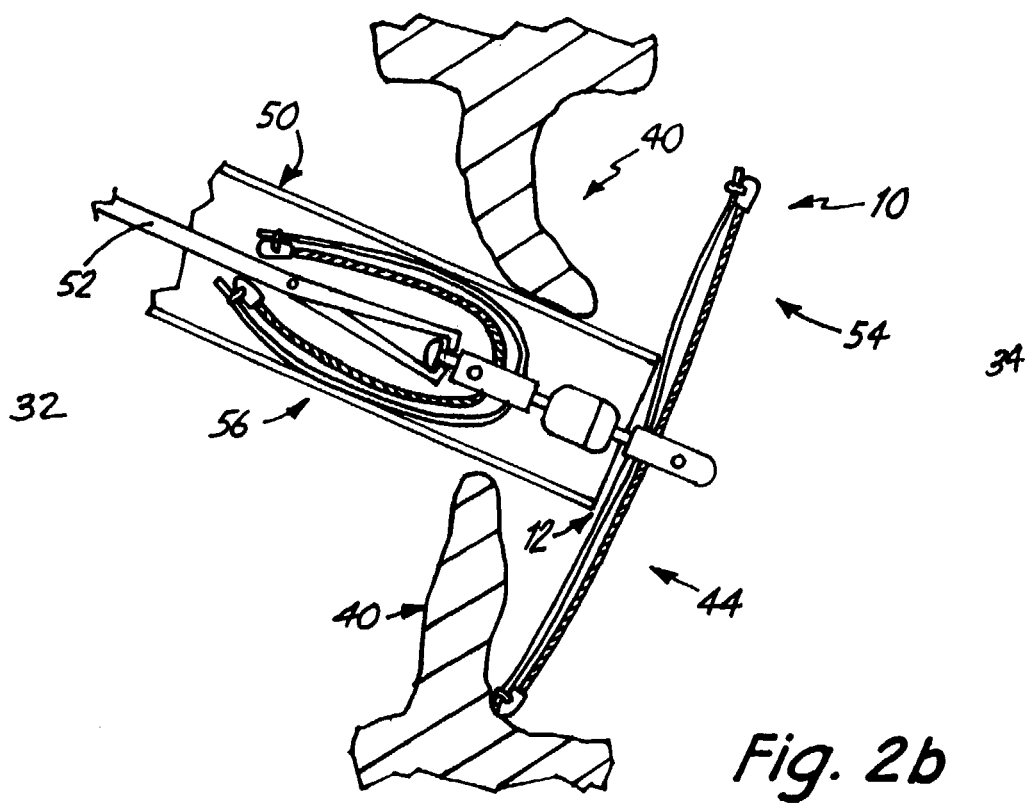
FIG. 2B is a diagram of an occlusion device being inserted into a defect.

FIG. 2B is a more detailed view of the septal wall 40 and the defect 44, shown between the right atrium 32 and the left atrium 34. Also shown is the occlusion device 10 of FIG. 1, a catheter 50, and a delivery forceps 52. As viewed in FIG. 2B, the occlusion device 10 comprises a distal side 54, a proximal side 56, and a center section 12. The occlusion device 10 is being inserted into the septal defect 44 from the catheter 50. The device 10 is tethered to the delivery forceps 52.

To insert the occlusion device 10, the catheter 50 is positioned proximate the septal defect 44. Next, the delivery forceps 52 is used to push the occlusion device 10 through the catheter 50 so that the distal side 54 of the device 10 unfolds in the left atrium 34. Although the distal side 54 has been deployed, the proximal side 56 is still folded in the catheter 50.

The placement of the catheter 50, or other means that guides the device 10 to the defect 44, determines the location of and angle at which the occlusion device 10 is deployed. Once the catheter 50 is properly positioned at the defect, the delivery forceps 52 is used to push the device 10 through the defect 44. The distal side 54 of the device 10 is then allowed to expand against septal walls 40 surrounding the defect 44.

In FIG. 2B, the center section 12 is articulated but the articulation remains inside the catheter 50 and is therefore immobilized. If the center section 12 of the occlusion device 10 is not articulated (or articulated but immobilized), the device's center section 12 must enter the defect 44 following the same angle of insertion as the catheter 50 or other delivery device. As a result, the insertion angle is limited by the catheter's angle of insertion FIG. 2B.

Often, due to limited space, the catheter 50 enters the heart at an angle that is not perpendicular to the defective wall FIG. 2B. In this situation, the device 10 cannot enter the defect 44 properly because the line of the center section 12 must follow the same line as the catheter 50. The device 10 must be forced into the defect 44 at an angle, which may cause the tissue surrounding the defect 44 to become distorted. If the surrounding cardiac tissue is distorted by the catheter 50, it is difficult to determine whether the device 10 will be properly seated once the catheter 50 is removed and the tissue returns to its normal state. If the device 10 is not seated properly, blood will continue to flow through the defect 44 and the device 10 may have to be retrieved and re-deployed. Both doctors and patients prefer to avoid retrieval and re-deployment because it causes additional expense and longer procedure time.

Figure 2C:
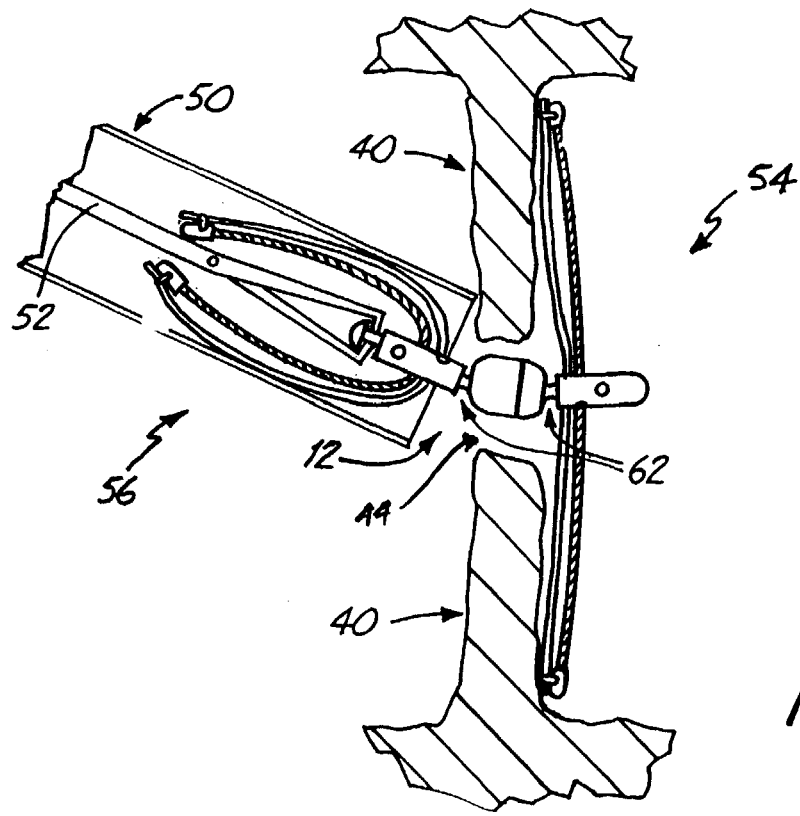
FIG. 2C is a diagram of an occlusion device with an articulated center section being inserted into a defect.

FIG. 2C shows an occlusion device 10 with an articulated center section 12 being inserted into a cardiac defect 44. Shown once again are the defect 44, septal walls 40, catheter 50, and occlusion device 10 comprising a distal side 54, and a proximal side 56. In FIG. 2C, the occlusion device 10 has been further advanced through the catheter 50 to expose the articulated center section 12 comprising a joint 62.

When the center section 12 is articulated or flexible, the insertion angle of the device 10 is not restricted to that of the catheter 50. The device 10 can be more easily inserted, because once the joint 62 is outside the catheter 50, the angle of insertion can be changed by allowing the joint 62 to move. This variable insertion angle allows the device 10 to enter the defect 44 at an optimum angle, minimizing distortion of surrounding cardiac tissue. If the tissue is not distorted when the device 10 is deployed, the seating of the device 10 should not change drastically once the catheter 50 is removed. Because the device 10 can be properly seated at the first insertion, the number of cases that require retrieval and redeployment should decrease.

Figure 2D:
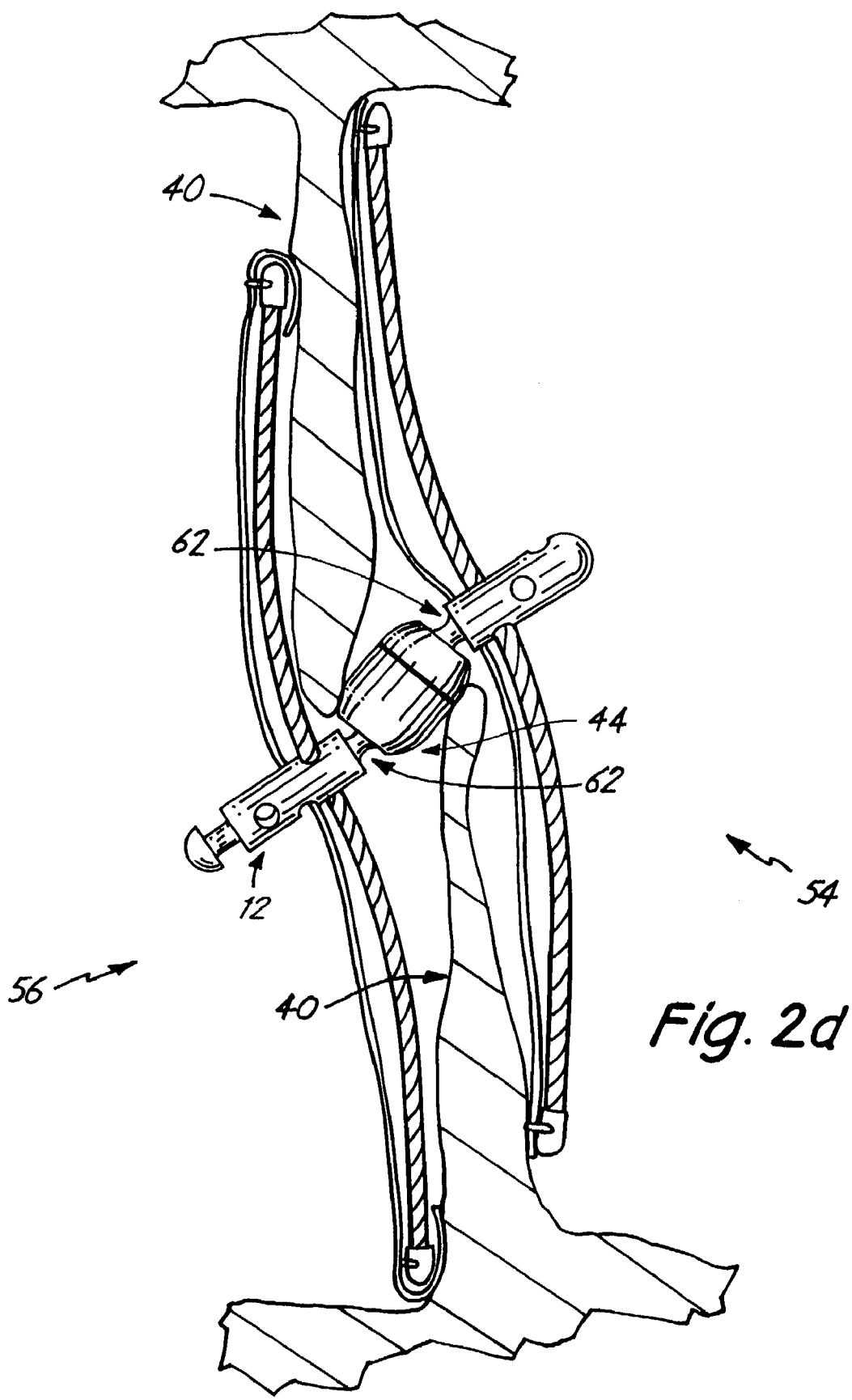
FIG. 2D is a diagram demonstrating the conformation capabilities of an occlusion device with an articulated center.

FIG. 2D shows an occlusion device 10 having an articulated center section 12 that is fully deployed and is occluding a cardiac defect 44. Shown in FIG. 2D is a distal side 54, a proximal side 56, a center post 12, a joint 62, septal walls 40, and a defect 44. The distal side 54 has been properly positioned, the proximal side 56 has been deployed and the device 10 has been released. FIG. 2D demonstrates the ability of an occlusion device 10 having an articulated center section 12 to conform to an irregularly shaped defect 44.

Another important advantage of the present invention is that the articulated center section 12 allows the distal and proximal sides 54, 56 to conform more readily to the contours of the heart 31 after it is deployed, providing a custom fit to a variety of defects. Often, when implanted, an occlusion device 10 is located in an irregularly shaped defect 44. Having an articulated center section 12 allows the occlusion device 12 to fit in a wider variety of defects, despite the shape or size of the defect.

For instance, as viewed in FIG. 2D, the septal wall 40 on the bottom of the defect may be only a few millimeters thick, but on the top may be many more millimeters thick FIG. 2D. In such cases, one side of the occluding device 10 may be bent open further than the other side. The side that is more distorted carries a high static load which both increases pressure on the surrounding tissue and increases the possibility of breakage of the device 10. If the center section 12 is articulated, it can bend such that the upper or lower fixation devices 14, 30 need not be the only the only parts which adjust to fit the defect 44. The ability to conform to a variety of heart contours provides better seating, reduces tension (increasing fatigue life), and decreases the likelihood of damage to tissue resulting from breakage and from pressure the device places on surrounding tissue.

Another feature of the occlusion device 10 is that it is fully retrievable. To allow the device 10 to be retrievable, as well as ensure that the device 10 fits into as small a diameter catheter as possible, it is important to ensure that the arms 16 are not of a length that results in the tips 18 clustering at the same location. If the tips 18 all occur at the same location when the device 10 is inside the catheter 50, the device will become too bulky to allow it to be easily moved through the catheter.

In situations where the occlusion device 10 is not properly deployed and must be retrieved into the catheter 50, it is possible to withdraw the occlusion device 10 back into the catheter 50 by grasping either the center section 12 or by grasping any one of the arms 16. When the device 10 is retrieved into the catheter 50, both the upper and lower arms 16 will be folded in the same direction. In such an instance, it is likewise important to vary the length of the upper arms from the length of the lower arms 16 so that when the device 10 is retrieved, the tips 18 on both the upper arms 16 do not cluster at the same location as the tips 18 on the lower arms 16.

Figure 3A:
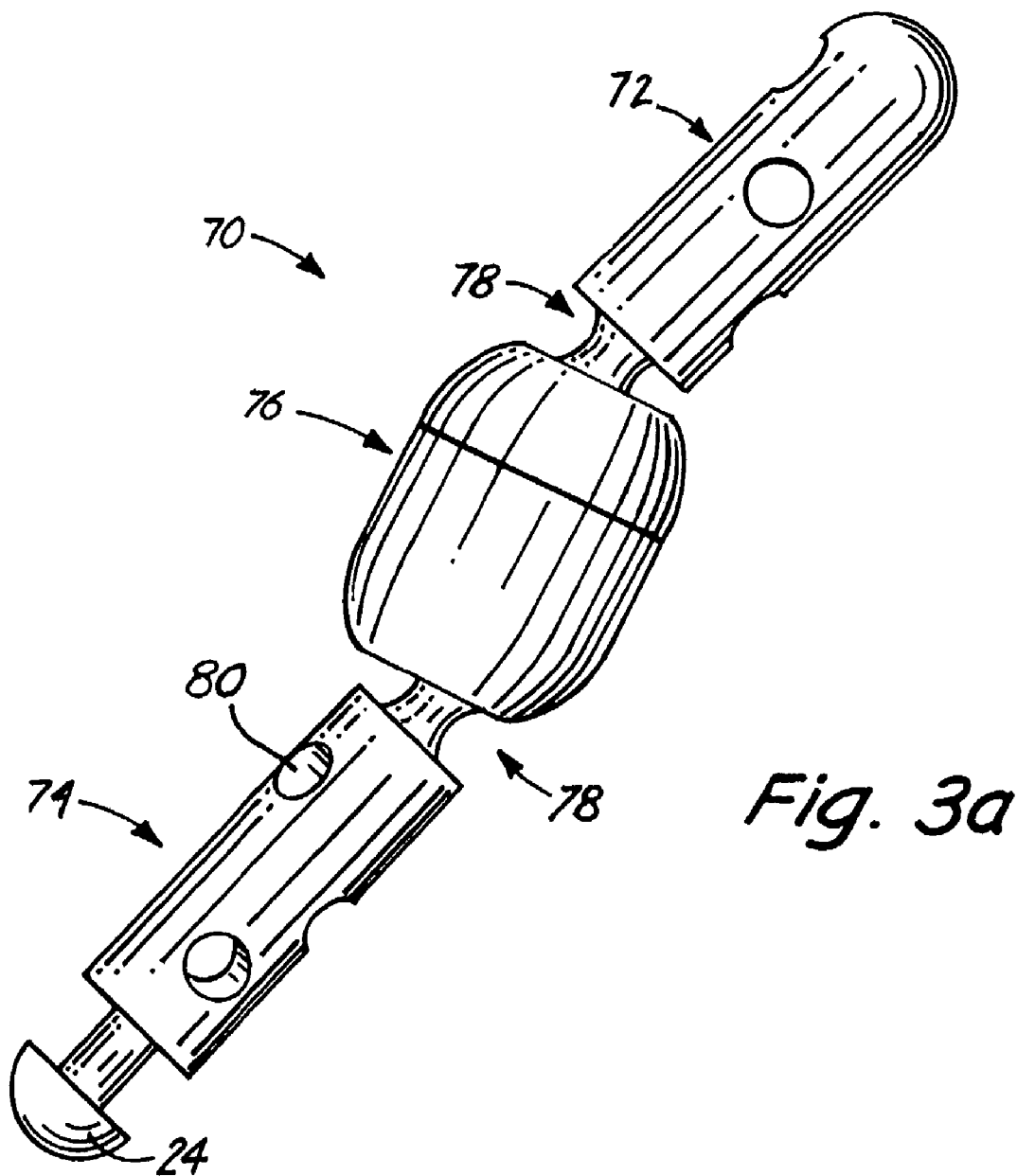
FIG. 3A is a side view of an articulated center section having two joints.

FIG. 3A is a perspective view of an example of an articulated center section 70 with double articulation. As viewed in FIG. 3A, the center section 70 comprises a right part 72, left part 74, and a center part 76. The left part 74 has a knob 24 located on one end. Both right and left parts 72, 74 have three holes 80 drilled through them. The center section 70 further comprise two joints or hinges 78 on each end of the center part 76. The joints or hinges 78 connect the right and left parts 72, 74 to the center 76 and allow for the right and left parts 72, 74 to rotate relative to the center part 76. The wire arms 16 (FIG. 1) attach to the center section by passing through the holes 80 drilled through the left and right parts 72, 74.

In this example, a joint 78 provides the articulation. Though shown with a double articulation, the articulated center section 70 is not so limited. The number of joints or hinges 78 may be varied to accommodate a particular defect or a particular type of defect. For example, one joint or hinge may be best for an atrial septal defect while two or three articulations may be best for a larger defect such as patent foramen ovale or a long defect such as patent ductus arteriosus.

The articulation may be achieved in a variety of ways. Ball joints or hinges may create the articulation. The articulation may also be created by the addition of a spring like coil to the center, a reduction of the amount of material used in a portion the center, or use of material that has ample flexibility when constructing the center.

Figure 3B:
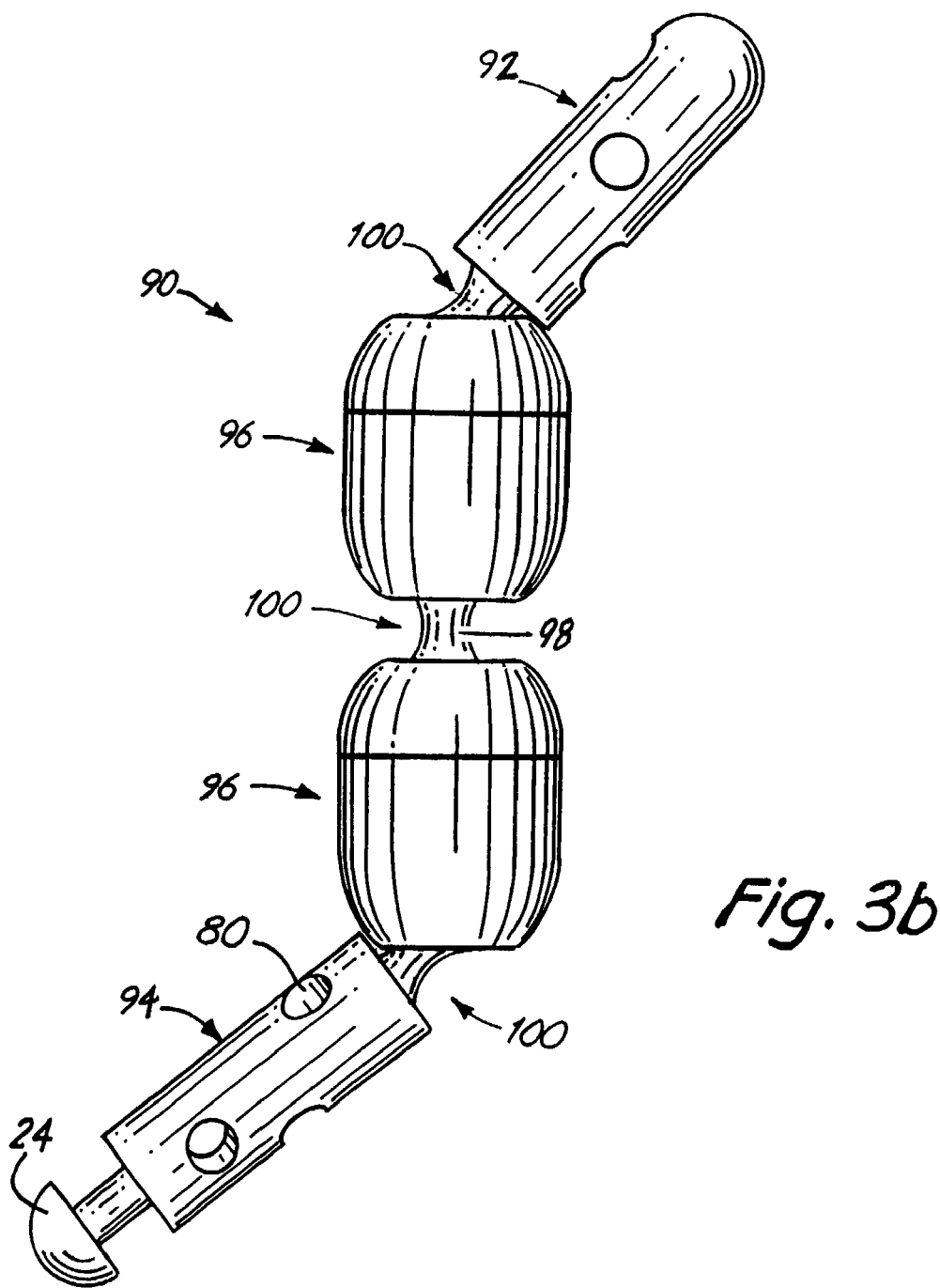
FIG. 3B is a side view of an articulated center section having three joints.

In addition, it is possible to provide the center section with more or less articulations. FIG. 3B is a side view of an articulated center section 90 with triple articulation, which demonstrates the range of flexibility of the joints 100. Shown is a right part 92, a left part 94 with a knob 24, two center parts 96, a joining part 98, and four joints 100. The large amount of flexibility allows the occlusion device to conform to a wide variety of defects. If less flexibility is needed, an center section 90 with one or two joints may be preferred.

Figure 4:
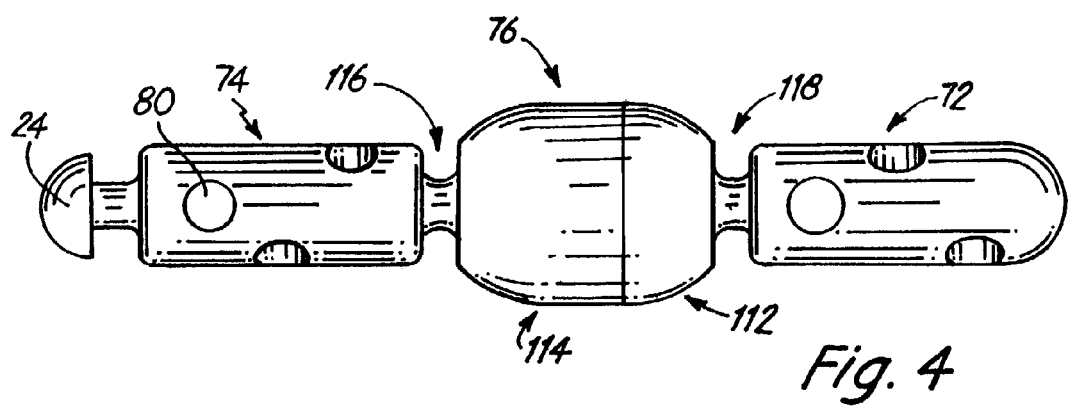
FIG. 4 is a side view of an articulated center section.

FIG. 4 is an enlarged side view of one example of an articulated center section 70, showing the section 70 in more detail. The articulated center section 70 is comprised of a right part 72, a left part 74 which has a knob 24, a center part 76, and two joints 116, 118. The center part 76 is comprised of a left sleeve 112 and a right sleeve 114. The left part 74 connects to center section 76 at the left joint 116. The right part 72 connects to the center part 76 at the right joint 118.

The joints or hinges 116, 118 allow the right and left parts 72, 74 to rotate relative to the center part 76, giving them a full 360° of motion relative to the center part 76. Preferably, the joints or hinges 116, 118 are designed to allow for maximum three dimensional movement of both the right and left parts 72, 74 relative to the center part 76. However, the joints 116, 118 may also be configured to provide two dimensional movement of the right and left parts 72, 74 relative to the center part 76. The range of motion need not be a full 360° to be an improvement. Other ranges of motion, such as two dimensional rotation may work also, depending on the type of defect.

Figure 5:
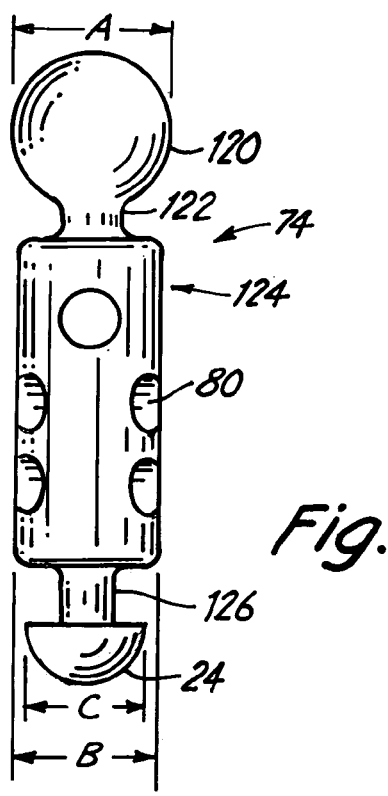
FIG. 5 is a side view of a left part of an articulated center section.

FIG. 5 is an enlarged side view of the left part 74. The left part 74 comprises a ball 120, a first neck 122, a cylindrical body 124, a second neck 126, a knob 24, and three holes 80. As described above, three holes 80 are drilled through the part 74 to allow for attachment of the wire arms 16.

The end ball 120 on one end of the left part 74 is connected to the cylindrical body 124 of the left part 74 at the first neck 122. The knob 24 is located on the other end of the cylindrical body 124 and is connected to the body 124 by a second neck 126. To assist in assembly, discussed in more detail below, the cylindrical body 124 of the left part 74 is preferably smaller in diameter than the ball 120. The knob 24 has a smaller diameter than both the body 124 and the ball 120. For example, the end ball 120 may have a diameter A of about 1.35 millimeters, the cylindrical body 124 may have a diameter B of about 1.2 millimeters, and the knob 24 may have a diameter C of about 1.0 millimeter.

The knob 24 is configured to allow a delivery forceps 52 to attach to the occlusion device 10 as it is pushed through the catheter 50 and allows the forceps to manipulate the device 10 as it is delivered. Likewise, a guide forceps can be used to position the occlusion device 10 once it reaches the desired location or to retrieve the device 10 should it not be seated properly. The knob 24 may additionally have a cross sectional area which allows the forceps to rotatably move the device while the device is inserted into a defect 44. The second neck 126 is grasped by a forceps so that there is at least some play between the forceps and the second neck 126 when pushing the device through a catheter. For example, the guide forceps may engage the second neck 126 by means of a claw-like or hook-like end. In an alternate embodiment, the knob 24 is threaded to allow for attachment to a threaded guide forceps.

Figure 6:
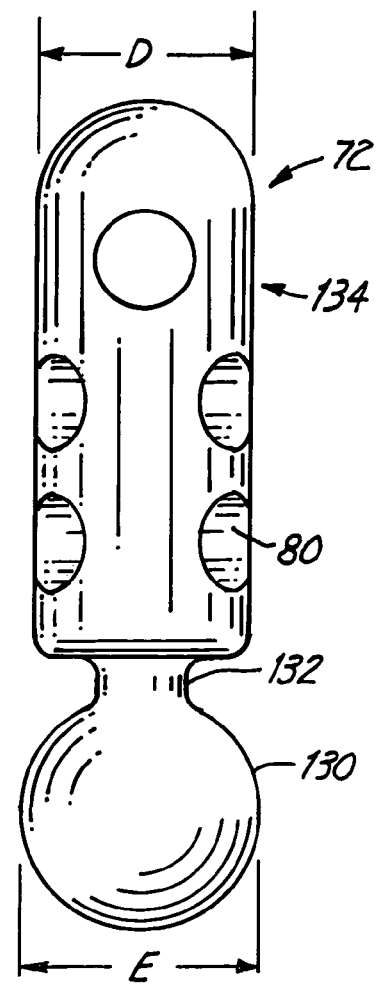
FIG. 6 is a side view of a right part of an articulated center section.

FIG. 6 is a side view of a right part 72. The right part 72 comprises a ball 130, a first neck 132, a cylindrical body 134, and three holes 80. Once again, three holes 80 are drilled through the part 72 to allow for attachment of the wire arms 16.

The right part 72 is nearly identical to the left part 74 except that it does not require a knob 24 or second neck 126. Because the occlusion device 10 only needs to be graspable at one end, a second knob is unnecessary. To assist in assembly, the cylindrical body 134 of the right part 72 is preferably smaller in diameter than the ball 130. For example, the end ball 130 may have a diameter D of about 1.35 millimeters, and the cylindrical body 134 may have a diameter E of about 1.2 millimeters.

Figure 7:
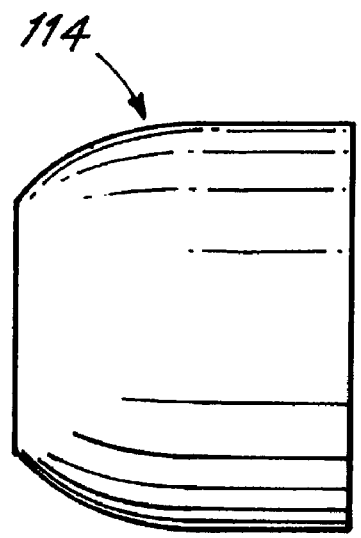
FIG. 7 is a side view of left and right sleeves.
Figure 7:
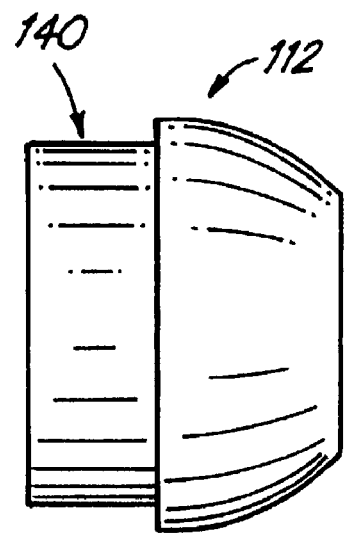

FIG. 7 is an exploded view of the center section. Shown is a right sleeve 112 and a left sleeve 114. The right sleeve 112 comprises a cuff 140. The cuff 140 is configured to fit inside the left sleeve 114 when the two sleeves are assembled. As shown more clearly on FIG. 8, the two sleeves 112, 114, once assembled, the two sleeves 112, 114 can be permanently attached at the cuff 140, and secured by welding.

Figure 8:
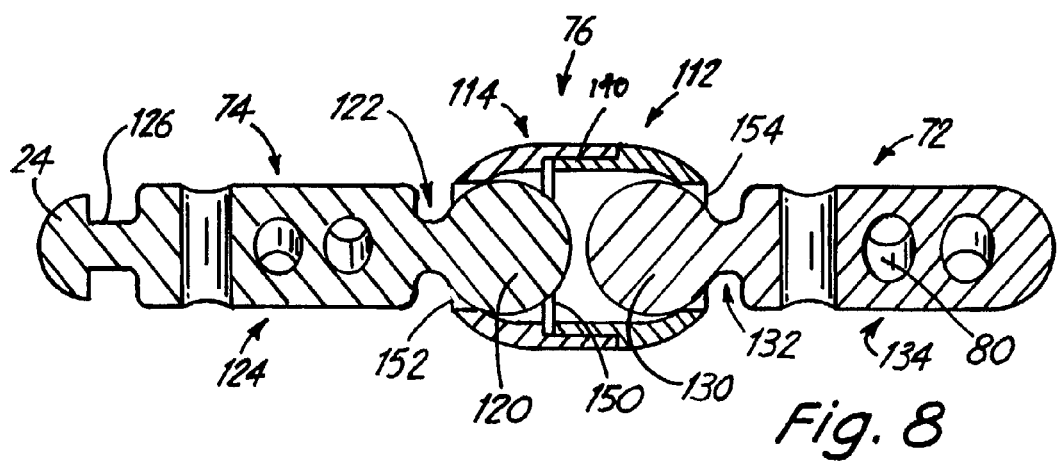
FIG. 8 is a cross sectional side view of an assembled articulated center section.

FIG. 8 shows a cross sectional view of an assembled articulated center post. Shown is the left part 74, the right part 72, and the center part 76, which comprises the left sleeve 114, and the right sleeve 112 having a cuff 140. Also shown is a washer 150. Each sleeve has a sleeve opening 152. Also shown are the details of the left and right parts: a knob 24, a second neck 126, first necks 122, 132, cylindrical bodies 124, 134, end balls 120,130, and holes 80. The sleeves 112, 114 have been welded together.

To assemble the center post, the left and right parts 74, 72 are slipped into the corresponding left and right sleeves 114, 112. As described above, the diameter of balls 120, 130 is less than the diameter of bodies 124, 134. As a result, the cylindrical bodies 124, 134 are small enough to fit through the sleeve openings 152, 154 but the end balls 120, 130 are too large to fit through the sleeve openings 152, 154. Once, the left part 74 is placed through the left sleeve 114, the cylindrical body 124 extends out the sleeve opening 152 but the end ball 120 remains inside the sleeve 114. Similarly, once the right part 72 is slipped through the right sleeve opening 154, the body extends out the sleeve 112 but the end ball 120 remains inside the sleeve 112. The washer 150 may be inserted at the end of the cuff 140 of the right sleeve 112. Next, the left sleeve 114 and the right sleeve 112 are joined by inserting the cuff 140 into the left sleeve 114. Once assembled, the sleeves 112, 114 are welded together.

The resulting assembly forms two ball joints which are able to rotate independently of each other relative to the center part 76. The first necks 122, 132 sit at the sleeve opening 152,154 after the cylindrical bodies 124, 134 have been pushed through the corresponding sleeve openings 152, 154. The diameters of the necks 122, 132 are smaller than the diameter of the sleeve openings 152, 154 so the necks 122, 132 have ample space to rotate freely in the sleeve openings 152, 154. The end balls 120, 130 are separated by the washer 150 so that they do not come in contact with each other and restrict each other's movement. The washer 150 also prevents the end balls 120, 130 from moving too far into the center of the sleeves 112, 114. If the end balls 120 were allowed to move too far back into the sleeves 112, 114, the left and right parts 74, 72 could also move into the sleeves 112, 114, thereby restricting the movement of the joints 116, 118. Preferably, a hard metal, such as titanium, is used to construct the parts of the center post because use of a hard material prevents binding within the ball joints.

There may be occasions where an occlusion device with single articulation or one joint is preferred. In one embodiment a neck 122, 132 is welded in place in the sleeve opening 152, or formed integrally, to immobilize one joint if only a single movable joint is desired. Alternatively, one of the end balls 120, 130 could be welded to the washer 150 to immobilize one of the joints.

Though shown in a patent foramen ovale occlusion device, an articulated center post can be adapted for use in any occluding device, including those designed for atrial septal defects, patent ductus arteriosus, and ventricular septal defects. The center post can also be adapted for use in an septal stabilization device.

Although the present invention has been described with reference to preferred embodiments, workers skilled in the art will recognize that changes may be made in form and detail without departing from the spirit and scope of the invention. In particular, any of the applicable features disclosed in related applications U.S. patent application entitled Septal Stabilization Device, Ser. No. 10/349,744, U.S. patent application entitled Hoop Design for Occlusion Device, Ser. No. 10/349,118, Occlusion Device Having Five or More Arms, Ser. No. 10/348,701, and U.S. patent application entitled Laminated Sheets for Use in a Fully Retrievable Occlusion Device, Ser. No. 10/348,864, filed on even date herewith, may be of use in the present invention. Each of these applications is hereby incorporated by reference.

What is claimed is:

1. A method of making an occlusion device with an articulated center section, the method comprising:
   forming a left part and a right part, each part comprising a body and a terminal end ball located on an end of the part, wherein the diameter of the ball is greater than the diameter of the body;
   inserting the left part into a left sleeve so that the terminal end ball sits inside the sleeve and the rest of the part comes out an opening in the sleeve;
   inserting the right part into a right sleeve so that the terminal end ball sits inside the sleeve and the rest of the part comes out an opening in the sleeve;
   connecting the left and right sleeves together to secure the terminal end balls inside the center sleeve;
   connecting a first occluding body to the left part; and
   connecting a second occluding body to the right part.

2. The articulated center section of claim 1, wherein each sleeve has a distal end opening smaller than the terminal end ball.

3. The articulated center post of claim 1, wherein the right sleeve has a cuff at the end which can be inserted into the left sleeve to connect the two sleeves.

4. An occlusion device comprising:
   a first occluding member;
   a second occluding member; and
   a center section allowing the first and second members to independently conform to an aperture, the center section comprising:
   a first part having a body connected to the first occluding member, a ball, and a neck connecting the ball to the body;
   a second part having a body connected to the second occluding member, a ball, and a neck connecting the ball to the body;

a first sleeve having an opening through which the neck of the first part extends and a socket in which the ball of the first part is movable; and a second sleeve having an opening through which the neck of the second part extends and a socket in which the ball of the second part is movable.

5. The occlusion device of claim 4, wherein the center section is made of titanium.

6. The occlusion device of claim 4, wherein the center section has a diameter of about 8 millimeters to about 0.1 millimeter.

7. The occlusion device of claim 4, wherein the center section has an axial length of less than about 20 millimeters.

8. The occlusion device of claim 4, wherein the first and second sleeves are joined together.

9. The occlusion device of claim 4, wherein a joint is connected between the first sleeve and the second sleeve.

10. An occlusion device comprising:
   a left center post including a body, a neck and a ball;
   a right center post including a body, a neck and a ball;
   a left sleeve having a socket that forms a joint with the ball of the left center post part and having an end opening smaller than the ball through which the neck of the left center post extends;
   a right sleeve having a socket that forms a joint with the ball of the right center post part and having an end opening smaller than the ball through which the neck of the right center post part extends;
   a left elastic shape memory fixation device attached to the body of the left center post part;
   a right elastic shape memory fixation device attached to the body of the right center post part; and
   a right sheet attached to the right fixation device.

11. The occlusion device of claim 10 and further comprising:
   a left sheet attached to the left fixation device.

12. The occlusion device of claim 10 wherein the right sleeve is attached to the left sleeve.

* * * * *